US012144577B1

(12) United States Patent
Schwartz et al.

(10) Patent No.: US 12,144,577 B1
(45) Date of Patent: Nov. 19, 2024

(54) MEDICAL DRAPE SYSTEM

(71) Applicants: Abraham Schwartz, San Juan, PR (US); Anwar Abdul-Hadi, San Juan, PR (US)

(72) Inventors: Abraham Schwartz, San Juan, PR (US); Anwar Abdul-Hadi, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 18/645,025

(22) Filed: Apr. 24, 2024

Related U.S. Application Data

(63) Continuation of application No. PCT/US2024/018507, filed on Mar. 5, 2024.

(51) Int. Cl.
*A61B 46/20* (2016.01)
*A61B 46/10* (2016.01)

(52) U.S. Cl.
CPC ............. *A61B 46/20* (2016.02); *A61B 46/10* (2016.02)

(58) Field of Classification Search
CPC ............ A61B 46/00; A61B 46/20; A41D 13/1236–129; A47H 2201/00; A47H 2023/003
See application file for complete search history.

(56) References Cited

U.S. PATENT DOCUMENTS

| | | | | |
|---|---|---|---|---|
| 2,252,359 | A * | 8/1941 | Wade | E06B 9/78 16/442 |
| 3,747,125 | A * | 7/1973 | Goldman | A61F 13/04 2/919 |
| 3,826,253 | A | 7/1974 | Larsh et al. | |
| 4,196,723 | A | 4/1980 | Moose, Jr. | |
| 4,336,797 | A * | 6/1982 | Latucca | A61B 46/00 128/854 |
| 5,562,107 | A | 10/1996 | Lavender et al. | |
| 7,214,185 | B1 | 5/2007 | Rosney et al. | |
| 8,011,371 | B2 | 9/2011 | Rotolo | |
| 11,517,388 | B2 | 12/2022 | Dine | |
| 2003/0009122 | A1 | 1/2003 | Veras | |
| 2006/0289121 | A1* | 12/2006 | Chen | E06B 9/262 160/89 |
| 2007/0235038 | A1 | 10/2007 | Alinsod et al. | |
| 2010/0275929 | A1* | 11/2010 | Kaska | A61B 46/00 128/852 |
| 2014/0008028 | A1* | 1/2014 | Rastegar | E06B 9/322 160/331 |

(Continued)

*Primary Examiner* — Keri J Nelson
*Assistant Examiner* — Seth R. Brown
(74) *Attorney, Agent, or Firm* — Patenting Consulting Group; Roberto J. Rios

(57) ABSTRACT

A simple and flexible drape arrangement is by provided including a cover and associated actuation mechanism to selectively cover and uncover a fenestration, the cover is coupled to a medical drape and the fenestration cover is under tension due to elastic filaments and operated via a tether that can be operated by mechanical or manual actuation, where neither of these methods, are dependent on the distance proximity of a medical practitioner's hands. The drape arrangement can also be attached to an existing fenestrated drape that can be easily carried in a sterile package in a field backpack. The drape arrangement conforms to a patient's body to permit the medical practitioner normal access to the body area.

44 Claims, 8 Drawing Sheets

(56) References Cited

U.S. PATENT DOCUMENTS

2015/0041284 A1\* 2/2015 Pfeiffer .................. B65G 13/07
198/790
2015/0359596 A1\* 12/2015 Jarrelle .................. A61B 46/20
128/854

\* cited by examiner

MEDICAL DRAPE SYSTEM

FIELD OF THE INVENTION

The present invention is directed to medical devices that reduce contamination over the surgical field when performing surgery under catastrophic ambient atmospheric conditions.

BACKGROUND OF THE INVENTION

Conducting surgical procedures in the field under extraordinary difficult conditions, such as the active battlefield, forest fires, volcano eruptions, and dust storms presents an elevated degree of risk to the patient. These scenarios not only compromise whatever level of sterility that can be obtained under the circumstances, but add exposure to toxicity of undefined particulate contamination in the ambient atmosphere.

To address this concern, U.S. Pat. No. 11,466,505 B1 granted on Oct. 11, 2022, to University of Puerto Rico, incorporated herein in its entirety by reference, provides a mechanism that is activated by the distance proximity of the surgeon's hands to the surgical fenestration in such a way as to open when the hands are closer than a predefined position, and close when the hands are further away from said position. This mechanism uses a support base for accommodating the fenestration and provides a convenient method of limiting atmospheric contamination at the surgical area when the surgeon is not actively engaged within the surgical area.

What is needed is a simple and flexible drape solution that is easily actuated to cover and uncover a surgical area.

SUMMARY OF THE INVENTION

The present invention provides a simple and flexible solution by providing a cover and associated actuation mechanism over a fenestration. Rather than having a fixed design support structure to accommodate the opening mechanism, the covering element is coupled to the medical drape and the fenestration cover is under tension and operated via a single tether.

According to an aspect of the invention, the tether can be operated by mechanical or manual actuation, where neither of these methods, are dependent on the distance proximity of a medical practitioner's hands.

According to another aspect of the invention, the drape arrangement provides a high degree of practicality and economic advantage since it is part of an existing medical drape and can be easily carried in a sterile package in a field backpack According to still another aspect of the invention, the drape arrangement is attached to an existing fenestrated drape that can be easily carried in a sterile package in a field backpack.

According to yet another aspect of the invention, the drape arrangement conforms to a patient's body to permit the medical practitioner normal access to the body area, rather than the mechanism of the drape being elevated above the patient.

According to an aspect of the invention, the drape arrangement is disposable along after completion of the surgical or medical procedure.

BRIEF DESCRIPTION OF DRAWINGS

Further features and advantages of the invention will become apparent from the following detailed description taken in conjunction with the accompanying figures showing illustrative embodiments of the invention, in which.

Figure 1:
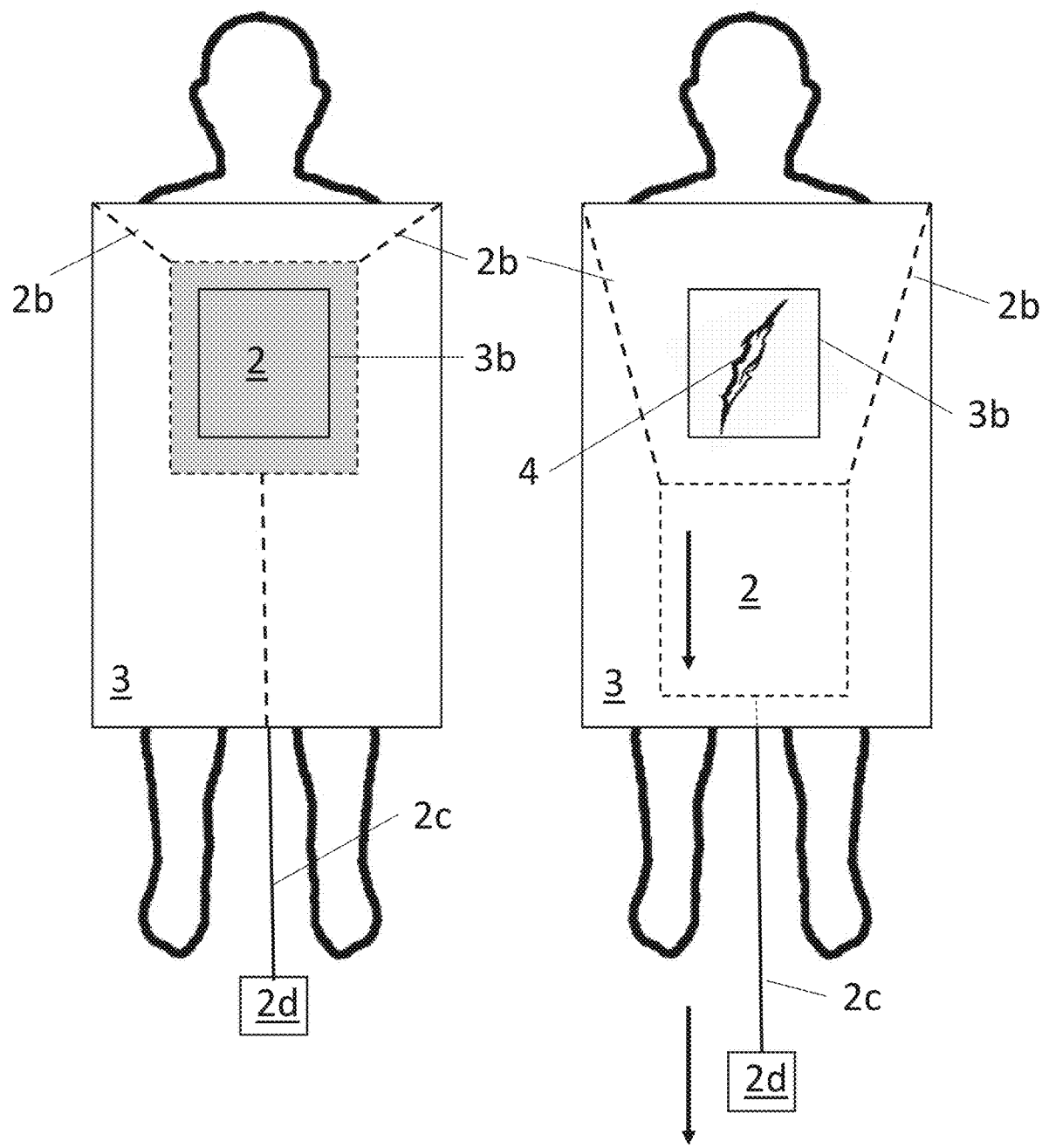
FIG. 1 illustrates the drape arrangement over a patient, according to an embodiment of the invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The drape arrangement of the present invention performs the basic task of covering and uncovering a body area to reduce contamination from the ambient atmosphere during a catastrophic event or when a medical practitioner is working on the body area. Also, by not relying on a supporting structure for the drape, the invention provides flexibility of the covering mechanism of the drape to conform to the shape of the patient. This also provides a closer working distance to a body area than when a mechanical support structure for the drape is used. In addition, the drape arrangement of the invention can be easily folded, sterile packaged, and carried in a backpack. The invention can be implemented using highly sophisticated prior art methods as well as using basic non-electrical mechanical mechanisms that are more suited to open field applications.

The term drape arrangement is interchangeably used throughout the description to refer to a fenestrated drape including the drape cover of the invention and also a drape cover of the invention that is configured to be attached or coupled to an existing fenestrated drape. Furthermore, the drape arrangement of the invention can be used for surgical and non-surgical applications and for medical or non-medical purposes. For the purpose of this invention, the term medical drape is used to mean drapes that are used in the medical field including, surgical applications and non-surgical applications such as but not limited to treatment of a body part.

As shown in FIG. 1 to FIG. 3B, the drape arrangement of the present invention is provided with three main layers of flexible sheets (1,2,3) to conform to the shape of the surgical or treating area of the patient. According to a preferred embodiment of the invention, the bottom sheet 1 has a fenestration 1b and is configured to be affixed to the patient so that the medical practitioner isolates and has access to the surgical or treating area. Preferably, the bottom sheet 1 is affixed to the patient by providing adhesive tape 1c on the lower surface of the bottom sheet 1 along the border of the fenestration 1b. The second flexible sheet is the cover sheet 2 and is attached via elastic filaments or cords 2b to either a top flexible sheet 3, the bottom sheet 1 or to both sheets 1 and 3. As can be appreciated, the top sheet 3, also has a fenestration 3b coinciding with the fenestration 1b of the bottom sheet 1. In addition, a non-stretch filament or cord 2c is attached to the cover sheet 2.

Figure 2A:
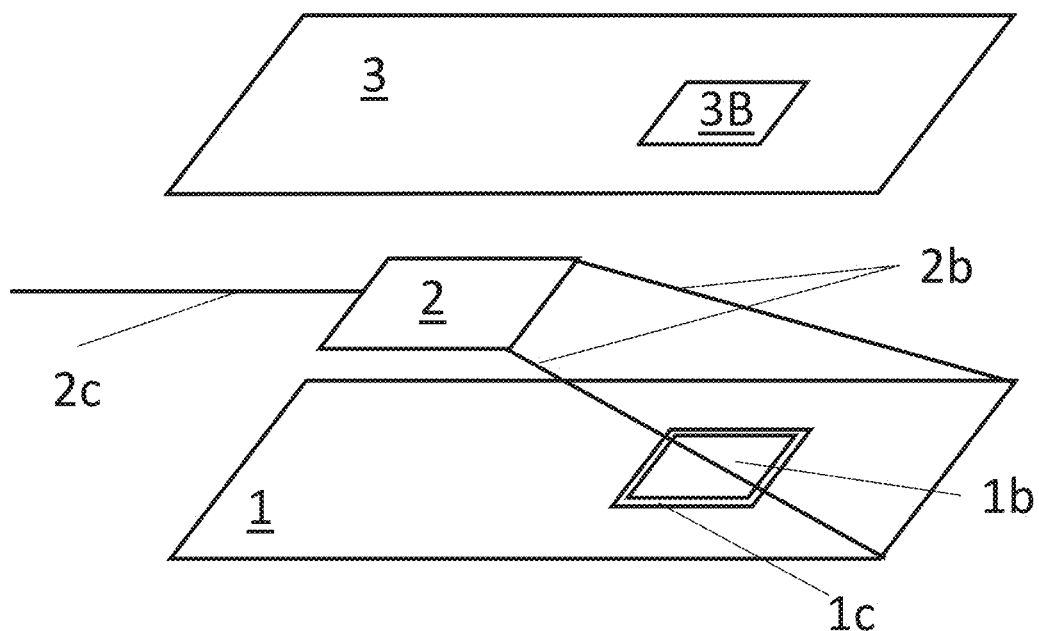
FIG. 2A shows an exploded view of the drape arrangement with the fenestration cover coupled to a bottom drape sheet, according to an embodiment of the invention.
Figure 2B:
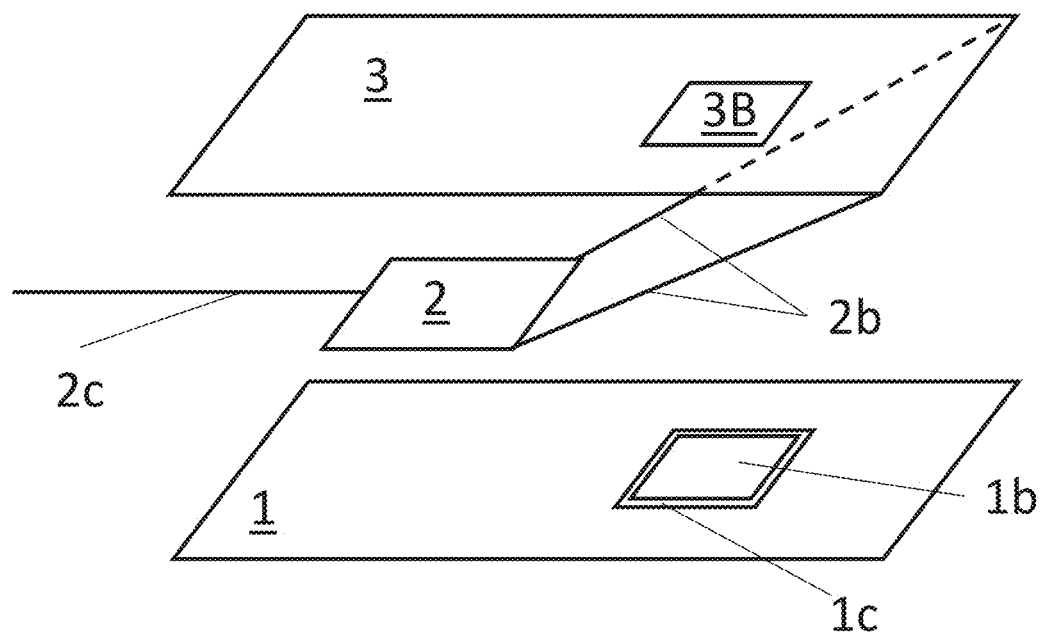
FIG. 2B shows an exploded view of the drape arrangement with the fenestration cover coupled to an upper drape sheet, according to an embodiment of the invention.

In a preferred embodiment, the elastic filaments or cords 2b are coupled to the adjacent corners of the cover sheet 2 and the non-stretch filament or cord 2c is coupled to the opposite side of the cover sheet 2 where the elastic filaments or cords 2b are coupled, as shown in FIG. 2A and FIG. 2B. As can be appreciated, the mechanism is actuated by pulling on the non-stretch filament or cord 2c to move the cover sheet 2 away from the fenestrations 1b and 3b into an open position where the fenestrations are uncovered. Pulling the non-stretch filament or cord 2c places tension on the elastic filaments or cords 2b. When tension on the non-stretch filament or cord 2c is released, the cover sheet 2 is pulled back over the fenestrations into its normally-covered position to cover the surgical or treating area.

Figure 3A:
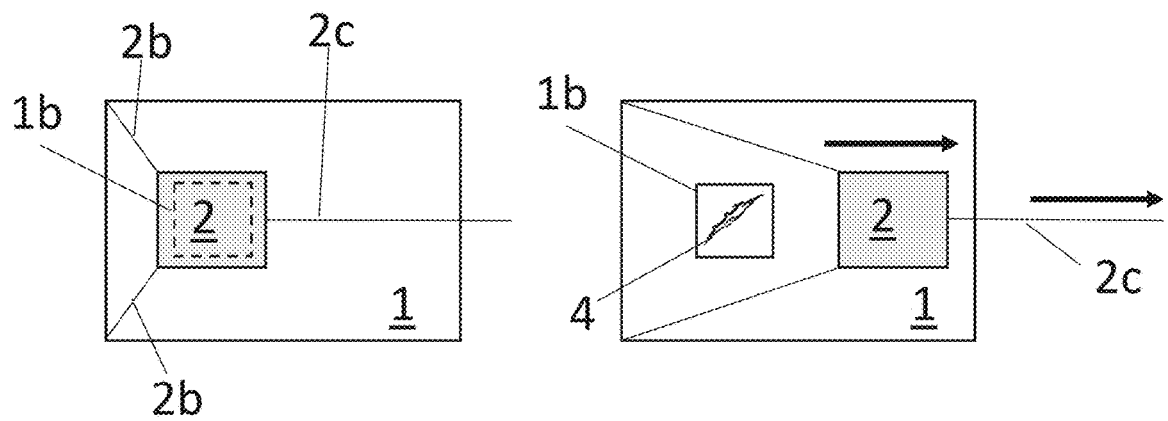
FIG. 3A shows the drape arrangement without the upper drape sheet to illustrate the cover covering and uncovering the fenestration and a wound, according to an embodiment of the invention.
Figure 3B:
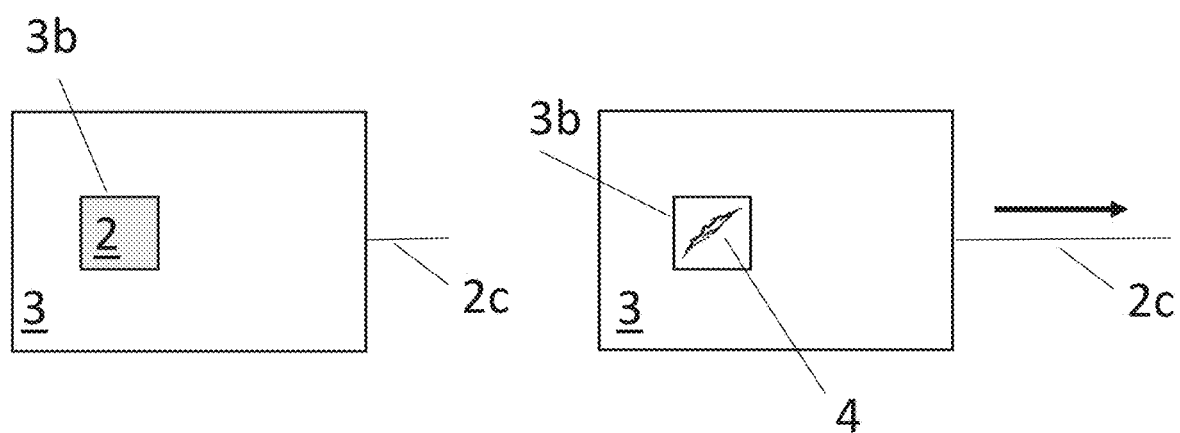
FIG. 3B shows a top view of the drape arrangement to illustrate the cover covering and uncovering the fenestration and a wound, according to an embodiment of the invention.

FIG. 3A shows the drape arrangement of the invention without the top sheet 3 to better understand the movement of the cover sheet 2 in relation to the fenestration 1b. However, it is to be understood that the cover sheet 2 moves between the bottom sheet 1 and the top sheet 3. When no tension is exerted on the non-stretch filament or cord 2c, the bottom fenestration 1b remains covered by the cover sheet 2 where the elastic filaments or cords 2b are in a rest state. When the non-stretch filament or cord 2c is pulled, the cover sheet 2 moves away from the fenestration 1b until the tension is ceased reaching a position where a part or all the fenestration 1b is uncovered. In practice, the surgical or treating area encompassed by the fenestrations 1b and 3b is covered by the cover sheet 2 so that when access into the area is needed (for example, to treat a body wound 4), the non-stretch filament or cord 2c is pulled uncovering the fenestration 3b, and as a consequence the fenestration 1b. As can be appreciated, the elastic filaments or cords 2b are hidden from the medical practitioner avoiding unwanted contact that might interrupt the movement of the cover sheet 2.

This drape arrangement of the invention can be deployed in two preferred embodiments. The first embodiment is with all the three sheets of flexible material coupled together as a unitary product as shown in FIG. 1 to FIG. 3B, where the dimensions of the bottom sheet 1 are provided to ensure that the patient is covered as required. Different versions of this embodiment are possible in terms of the size and shape of the fenestration, as well as the bottom sheet to accommodate different categories of surgery. The second embodiment is configured with only the top sheet 3 and the cover sheet 2 connected as a unitary product configured to be attached to a standard surgical fenestrated drape such that the fenestration 3b of the top sheet 3 is placed and aligned over the fenestration of the standard surgical drape and secured thereto. This arrangement is the same as the one illustrated in FIG. 2B, with the exception that the bottom sheet 1 is now a standard surgical fenestrated drape independent from the unitary product of the top sheet 3 and the cover sheet 2. This mode can be adapted to a verity of different standard surgical drapes and is easier to carry into the field. In this exemplary embodiment, at least one border of the top sheet 3 is provided with adhesive tape so that a lower surface of the unitary drape arrangement is secured to an upper surface of the standard surgical drape.

Figure 4A:
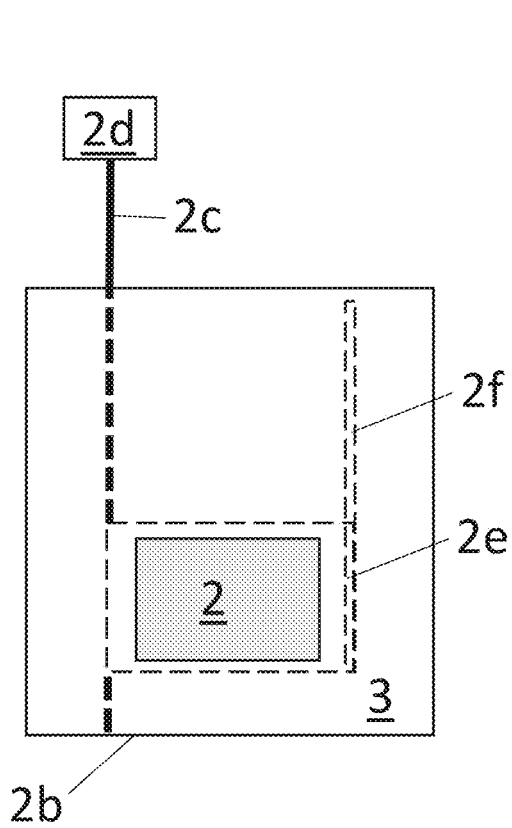
FIG. 4A shows the drape arrangement in a normally-covered position using a single elastic filament, according to an embodiment of the invention.
Figure 4B:
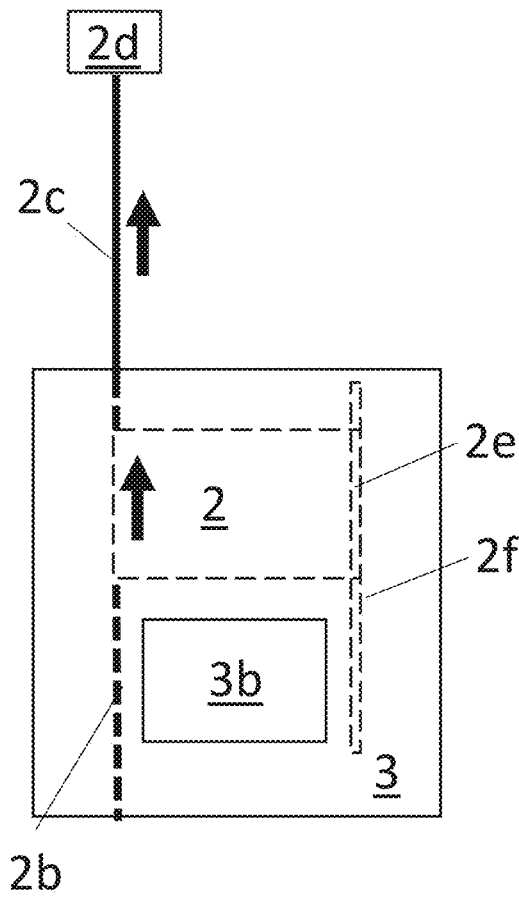
FIG. 4B shows the drape arrangement in an uncover position using a single elastic filament, according to an embodiment of the invention.
Figure 4C:
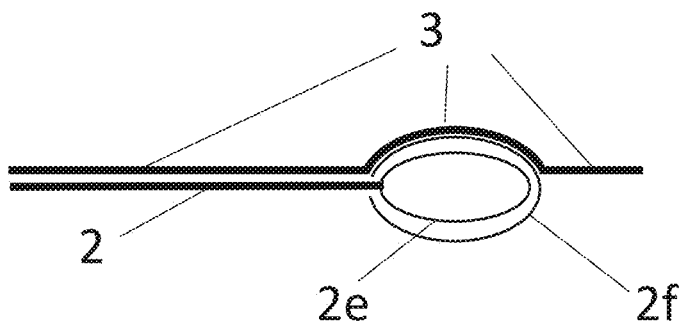
FIG. 4C illustrates a sliding arrangement for the cover of the drape arrangement using a single elastic filament, according to an embodiment of the invention.

According to another embodiment of the invention, the drape arrangement can also be provided with a single elastic filament or cord 2b as shown in FIG. 4A and FIG. 4B. The elastic filament or cord 2b is coupled to a corner of the second sheet 2 and the non-stretch filament or cord 2c is coupled to the other side of the cover sheet 2 at a corner opposite to the corner where the elastic filament or cord 2b is coupled as shown in FIG. 4A. In an exemplary arrangement, a side end of the cover sheet 2 is provided with a flexible tab 2e that is inserted into a flexible rail 2f (FIG. 4C) so that the flexible tab 2e slides inside the flexible rail 2f when the cover sheet 2 is moved to cover and uncover the fenestrations 1b and 3b, as shown in FIG. 4A and FIG. 4B. While FIG. 4C illustrates the flexible rail 2f coupled to the top sheet 3, it is envisioned that the flexible rail 2f can be coupled to the bottom sheet 1 or to both the top sheet 3 and the bottom sheet 1. The flexible tab 2e and the flexible rail 2f are made from a flexible material so that flexible sheets conform to the shape of the surgical or treating area of the patient.

Figure 5A:
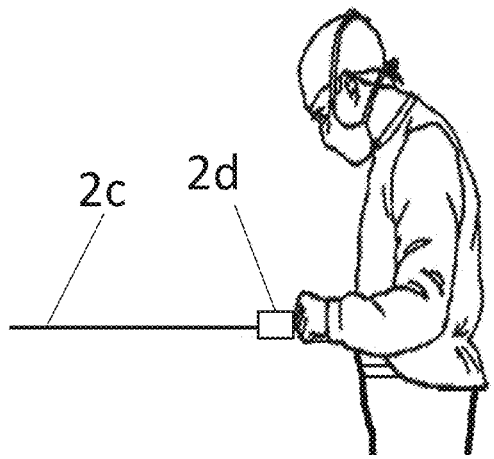
FIG. 5A illustrates a medical practitioner manually actuating and holding a handle of the pulling cord, according to an embodiment of the invention.
Figure 5B:
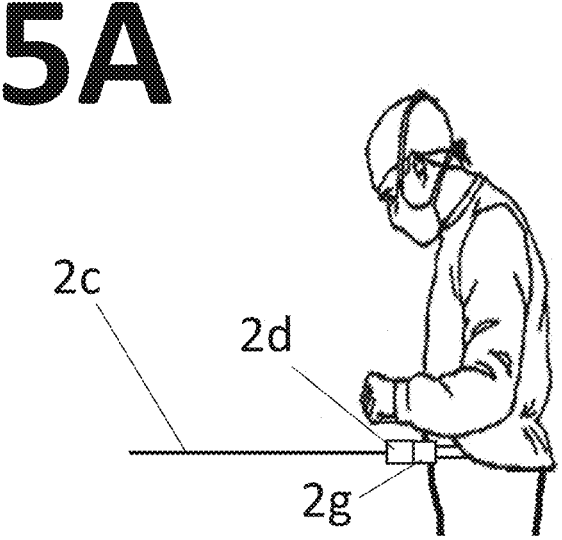
FIG. 5B illustrates a handle of the pulling cord maintained in an actuated state by a holding mechanism coupled to a medical practitioner, according to an embodiment of the invention.
Figure 5C:
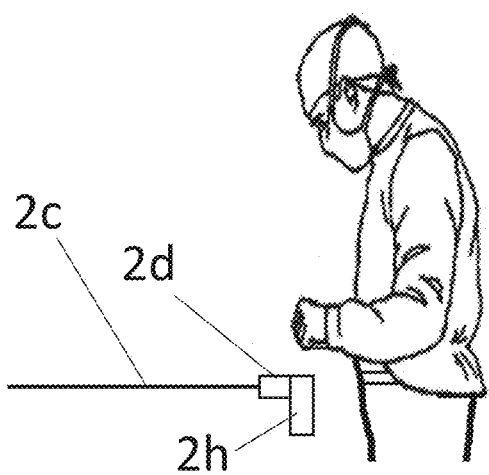
FIG. 5C illustrates a handle of the pulling cord maintained in an actuated state by a holding mechanism independent of a medical practitioner, according to an embodiment of the invention.

In operation, the simplest and most basic version of the invention is to have a medical practitioner or an assistant selectively opening and closing the fenestration by pulling and releasing a handle 2d coupled to the non-stretch filament or cord 2c by hand, as shown in FIG. 5A. However, other embodiments provide a holding mechanism that maintains the non-stretch filament or cord 2c pulled and the fenestrations uncovered without the need of the medical practitioner or the assistant constantly holding the handle 2d by hand. As shown in FIG. 5B, the handle 2d can be removably attached to a holding mechanism 2g that is worn or attached to the medical practitioner or assistant. In an exemplary embodiment, the holding mechanism 2g can be attached or be part of a belt or a piece of clothing of the medical practitioner or the assistant. In an alternate embodiment, the a holding mechanism 2h is provided independent from the medical practitioner or assistant, as illustrated in FIG. 5B. For example, the holding mechanism 2h can be provided on a stand where the handle is removably secured.

Figure 6:
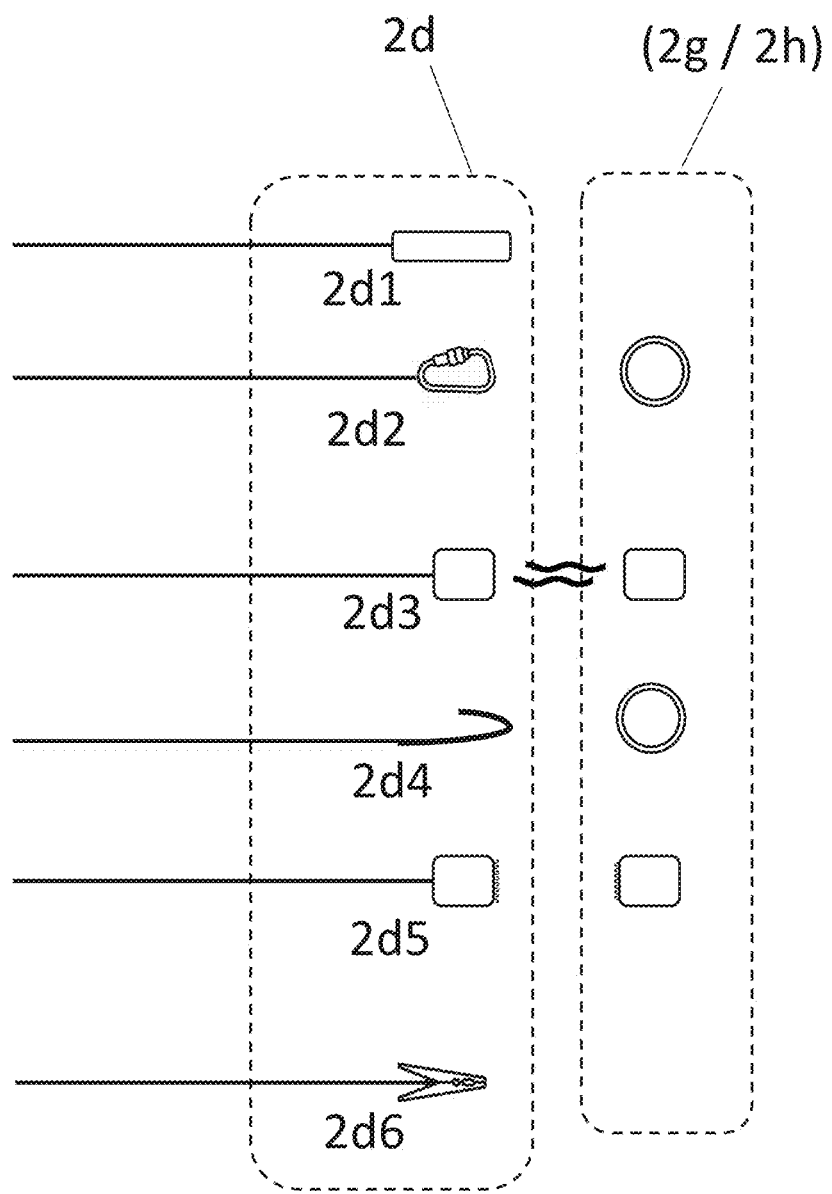
FIG. 6 shows various handles and their associated holding mechanisms, according to embodiments of the invention.

FIG. 6 shows various examples of handles 2d and holding mechanisms 2g and 2h, according to preferred embodiments of the invention. At the outset, it can be appreciated that all the handles 2d1-2d6 can be manually pulled and hold by the medical practitioner or the assistant even if the handle is also secured to a holding mechanism 2g or 2h. Handle 2d1 is the most basic embodiment which only requires the handle 2d to be large enough for adequate grasping by a hand. In another embodiment, handle 2d is provided as a carabiner 2d2 coupled to the non-stretch filament or cord 2c. In this embodiment, a complementary ring can be provided either as a holding mechanism 2g coupled to the medical practitioner or the assistant or as a holding mechanism 2h independent from the medical practitioner or the assistant, as previously explained. In operation, the non-stretch filament or cord 2c is pulled by the carabiner 2d2 and securely engaged to the complementary ring once the fenestration is uncovered. When the fenestration needs to be covered, the carabiner 2d2 is disengaged from the complementary ring so that the elastic filaments or cords 2b return the cover sheet to its original position covering the fenestration. According to another embodiment, the handle 2d is provided as a magnet 2d3 coupled to the non-stretch filament or cord 2c. In this embodiment, a complementary magnet can be provided either as a holding mechanism 2g coupled to the medical practitioner or the assistant or as a holding mechanism 2h independent from the medical practitioner or the assistant, as previously explained. In operation, the non-stretch filament or cord 2c is pulled by the magnet 2d3 and magnetically engaged to the complementary magnet once the fenestration is uncovered. When the fenestration needs to be covered, the magnet 2d3 is disengaged from the complementary magnet so that the elastic filaments or cords 2b return the cover sheet to its original position covering the fenestration. In addition, the handle 2d can be provided as a hook 2d4 coupled to the non-stretch filament or cord 2c. In this embodiment, a complementary ring can be provided either as a holding mechanism 2g coupled to the medical practitioner or the assistant or as a holding mechanism 2h independent from the medical practitioner or the assistant, as previously explained. In operation, the non-stretch filament or cord 2c is pulled by the hook 2d4 and magnetically engaged to the complementary ring once the fenestration is uncovered. When the fenestration needs to be covered, the hook 2d4 is disengaged from the complementary ring so that the elastic filaments or cords 2b return the cover sheet to its original position covering the fenestration. In another embodiment, the handle 2d is a hook and loop fastener 2d5 coupled to the non-stretch filament or cord 2c. In this embodiment, a complementary hook and loop fastener is provided either as a holding mechanism 2g coupled to the medical practitioner or the assistant or as a holding mechanism 2h independent from the medical practitioner or the assistant, as previously explained. In operation, the non-stretch filament or cord 2c is pulled by the hook and loop fastener 2d5 and fastened to the complementary hook and loop fastener once the fenestration is uncovered. When the fenestration needs to be covered, the hook and loop fastener 2d5 is unfastened from the complementary hook and loop fastener so that the elastic filaments or cords 2b return the cover sheet to its original position covering the fenestration. Also, the handle 2d is a clip 2d6 coupled to the non-stretch filament or cord 2c. In this embodiment, the clip 2d6 is clipped to a holding mechanism 2g coupled or worn by the medical practitioner or the assistant or to a holding mechanism 2h independent from the medical practitioner or the assistant, as previously explained. In operation, the non-stretch filament or cord 2c is pulled by the clip 2d6 and clipped once the fenestration is uncovered. When the fenestration needs to be covered, the clip 2d6 is unclipped so that the elastic filaments or cords 2b return the cover sheet to its original position covering the fenestration. It should be understood that other types of handles are encompassed by the present invention to the extent that the handles are configured to be grasped and pull by a person and removably hold by a holding mechanism. In addition, other variations are possible as the positions of the handle and the holding mechanism can be inverted. For example, a handle 2d can be a ring with a complementary hook or carabiner provided as the holding mechanisms 2g or 2h.

In the previous embodiments, the non-stretch filament or cord 2c is manually pulled by a person using a handle 2d. However, according to other embodiments, the non-stretch filament or cord 2c can also be actuated by a mechanical pulling mechanism directly coupled to the non-stretch filament or cord 2c so that actuation of said mechanical pulling mechanism pulls the non-stretch filament or cord 2c to selectively cover and uncover the fenestrations.

Figure 7:
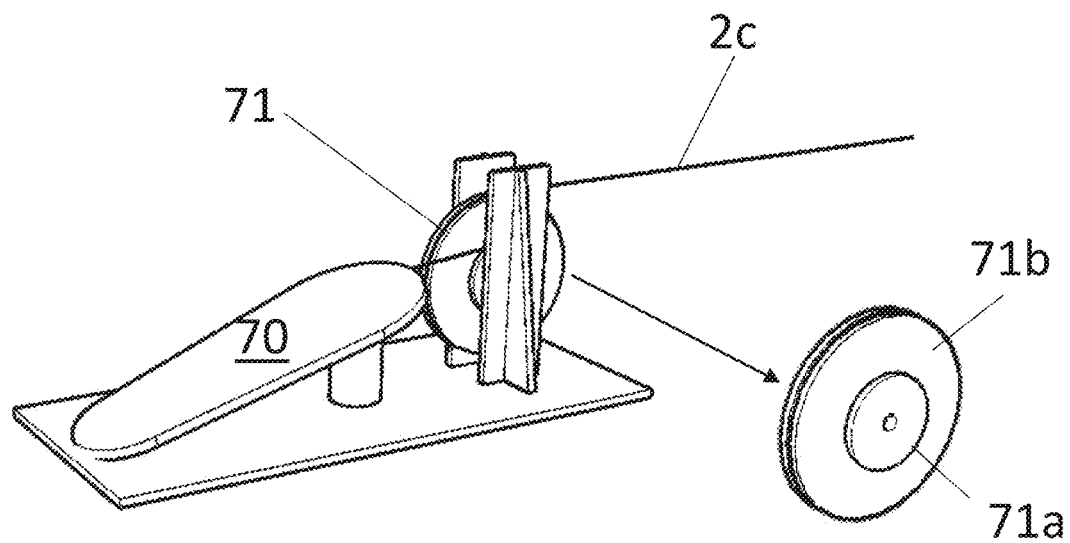
FIG. 7 shows a remote actuation mechanism for the pulling cord, according to an embodiment of the invention.
Figure 8:
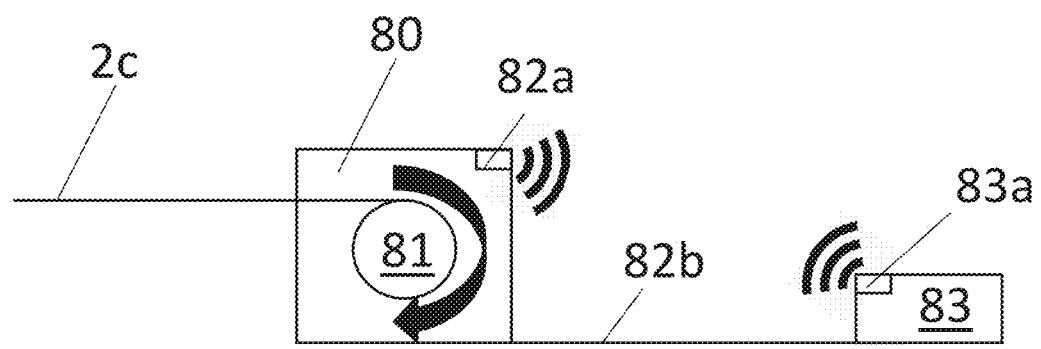
FIG. 8 shows another remote actuation mechanism for the pulling cord, according to an embodiment of the invention.

FIG. 7 illustrates an embodiment where the mechanical pulling mechanism is a foot pedal 70 that winds/unwinds a double spool 71. For example, if the ratio of the small spool 71a diameter to the large spool 71b diameter is 3 to 10, then pressing the foot peddle causes the double spool to rotate a full turn, so that a non-stretch filament attached around the small spool moves approximately 9.4 cm and a non-stretch filament attached around the larger spool would move approximately 31.4 cm. This mechanical advantage would be enough to cause the cover sheet to open and close the fenestration. This mechanical version of the invention does not require electricity.

However, in accordance to other embodiments of the invention, the non-stretch filament or cord 2c can also be actuated by a motor directly coupled to the non-stretch filament or cord 2c so that actuation of the motor pulls the non-stretch filament or cord 2c to selectively cover and uncover the fenestrations. In a preferred embodiment, the non-stretch filament or cord 2c is wound on a spool 81 that is coupled to a rotating shaft of an electric motor 80 so that the non-stretch filament or cord 2c is selectively pulled and the fenestration is cover and uncovered when the motor is rotated, as in the previous embodiments. The motor 81 can be actuated by a remote actuator 83 via a wired connection 82b (such as but not limited to a cable), a wireless connection 82 (such as but not limited to WIFI, Bluetooth, Infra-Red, RF), or a combination of both types of connections. In a preferred embodiment, the remote actuator 83 is a foot pedal that transmits a wired electrical signal through a cable 82b, or a wireless signal via transmitting/receiving units 82a and 83a, or a combination of both types of signals.

Figure 9:
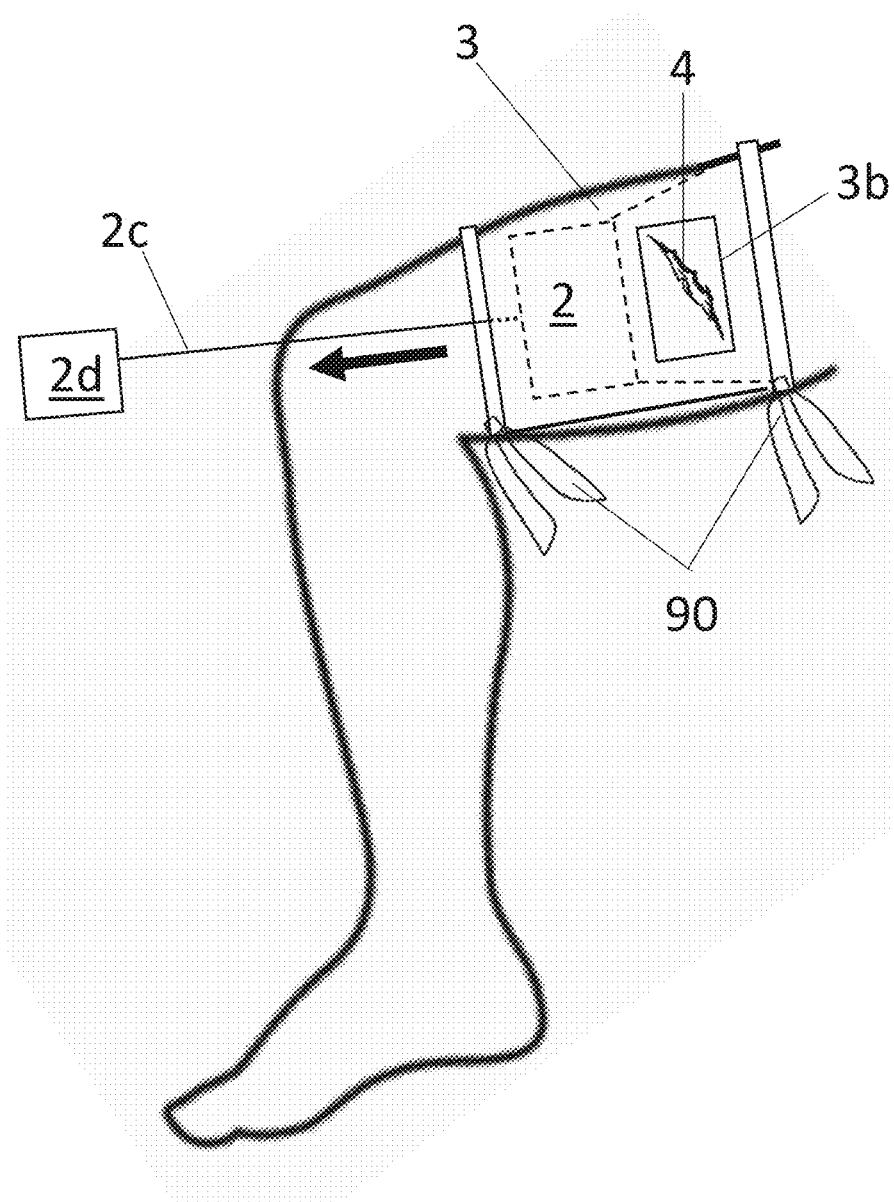
FIG. 9 shows the surgical drape on a patient's leg, according to an embodiment of the invention.

The drape arrangement of the present invention can also be used when considering serious injuries to the arms or legs occurring in the field. This embodiment is still consistent with the arrangement of three sheets of flexible material previously described, but the arrangement conforms to a smaller area than the core body of the patient (for example a smaller drape of 6×6 inches with the a 4×4 inches fenestration) like the one shown in FIG. 1. To accommodate this difference, straps 90 are provided at the top and bottom ends of the drape arrangement to secure and seal the arrangement against the body part, as shown in FIG. 9, where adhesive tape can be also used to adhere the lateral sides of the drape arrangement to the clothing or the skin of the injured person. These straps 90 also serve as adjustable torniquets to control the blood flow to an injured area while attending an injury. By cutting away the clothing from the injured extremity and covering the extremity with the drape arrangement of the invention, the injury and surrounding area can be continually observed while in transport and protected from ambient contamination. Moreover, the injury area may be rapidly made available to the medical personnel by quickly covering and uncovering the fenestration over the injury with a minimal disruption and discomfort to the patient by releasing the tension on the filament or cord, and applying tourniquet pressure by tightening the proximal strap on the invention.

The following examples demonstrate how the invention would be employed in specific situations under contaminated ambient atmosphere.

The basic version of the invention would have a plastic cover sheet, such as but not limited to polyethylene, larger than the fenestrations of the top and bottom sheets. The rectangular cover sheet would be attached to two or more elastic ribbons or cords to one side with a non-stretch filament, such as but not limited to a monofilament string, attached to the opposite side of the cover sheet. The other ends of the elastic filaments or cords are attached to the plastic top and bottom sheets, while the non-stretch filament or cord is lead through the top and bottom sheets. The arrangement could be similar to using a polyethylene resealable bag to serve as the top and bottom sheets with a fenestration cut in both layers of the desired size and shape. The fenestration cover sheet would be positioned inside the resealable bag and the elastic filaments or cords attached towards the opening of the bag and the non-stretch filament or cord lead through a hole in the bottom of the bag to be pulled and released by hand. This basic version of the invention could be sterilized and placed in a larger resealable bag for storage before use.

In another example, an assistant would be responsible to open and close the fenestration over the surgical area, as required by a surgeon, by pulling and releasing the tension on the non-stretch filament or cord. The resealable bag may then be directly attached to the patient by double-sided adhesive tape around the fenestration and the outer edges of the resealable bag such that it covers the surgical area and areas beyond, as necessary.

The sheets used in the invention are made from materials with specific characteristics. These include flexibility to contour to the surface of the patient, low surface friction in order to slide over each other, transparency to monitor the surgical or treatment area and surrounding area of the patient, ability to withstand conditions of sterilization, and the ability to bond to themselves and other materials, such as the elastic ribbons, strings or cables and non-stretch filaments or cables. The elastic filaments or cords must be firm and able to stretch with just the necessary force to open the fenestration but also have adequate resiliency to return back to the same length to consistently close the fenestration. The non-stretch filament or cord must have a very low extension coefficient to ensure and maintain the distance the cover sheet moves to open and close the fenestration. The adhesive tape used in some embodiments, can be a double stick tape that provides a robust bond to the sheeting materials such that the drape sheets of the drape arrangement are hold together, binds to the patient and/or to a standard surgical drape during use.

The number of elastic filaments or cords providing the tension to the cover sheet can be one or more. However, in a preferred embodiment, the optimum number of elastic filaments or cords is two on one side attached to the corners of the cover sheet and at an angle to the top or bottom sheets to provide a balanced force to maintain smooth, straight consistent motion over the fenestration. Equally, the number of non-stretch filaments can be one or more, with the optimum number being one attached to the middle of the side opposite the elastic filaments or cords of the cover sheet to maintain smooth, straight motion over the fenestration.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A fenestrated drape system comprising:
a first drape sheet having a first passthrough opening;
a second drape sheet having a second passthrough opening;
a third drape sheet positioned between said first drape sheet and said second drape sheet, said third drape sheet being the only drape sheet provided between said first drape sheet and said second drape sheet;
at least one elastic cord coupling said third drape sheet to at least one of the first drape sheet or the second drape sheet, wherein a first end of said at least one elastic cord is the only portion of said at least one elastic cord in contact with said third drape sheet; and
at least one pulling cord coupled to said third drape sheet so that the third drape sheet is configured to uncover both said first passthrough opening and said second passthrough opening when the pulling cord is actuated.

2. The fenestrated drape system of claim 1, wherein the third drape sheet is configured to slide between said first and second drape sheets to uncover both said first and second passthrough openings.

3. The fenestrated drape system of claim 1, wherein said third drape sheet returns to an original position covering both said first and second passthrough openings when the at least one pulling cord is not actuated.

4. The fenestrated drape system of claim 1, comprising two elastic cords coupling said third drape sheet to said at least one of the first drape sheet or the second drape sheet.

5. The fenestrated drape system of claim 4, wherein second ends of the two elastic cords are respectively coupled to opposite locations of an end of said at least one of the first drape sheet or the second drape sheet, and first ends of the two elastic cords are respectively coupled to opposite locations of an end of said third drape sheet.

6. The fenestrated drape system of claim 1, wherein a second end of said at least one elastic cord is coupled to an end of said at least one of the first drape sheet or the second drape sheet.

7. The fenestrated drape system of claim 6, wherein said at least one pulling cord is coupled to another end of said third drape sheet, opposite to the end of the third drape sheet when said at least one elastic cord is coupled.

8. The fenestrated drape system of claim 1, wherein said at least one pulling cord is non-stretchable.

9. The fenestrated drape system of claim 1, wherein said at least one pulling cord comprises a handle configured to be manually actuated.

10. The fenestrated drape system of claim 1, further comprising a mechanical pulling mechanism coupled to said at least one pulling cord so that actuation of said mechanical pulling mechanism by a user causes said at least one pulling cord to selectively cover and uncover both said first and second passthrough openings.

11. The fenestrated drape system of claim 10, wherein said mechanical pulling mechanism comprises a spool where said at least one pulling cord is wound.

12. The fenestrated drape system of claim 11, wherein said spool is coupled to a pedal.

13. The fenestrated drape system of claim 11, wherein said spool is coupled to a motor.

14. The fenestrated drape system of claim 13, wherein said motor is actuated at least by one of a wired actuator or a wireless actuator.

15. The fenestrated drape system of claim 13, wherein said at least one of a wired actuator or a wireless actuator is a pedal.

16. The fenestrated drape system of claim 9, wherein said handle comprises at least one of: a magnet, a carabiner, a hook and loop fastener, a clip or a hook.

17. The fenestrated drape system of claim 1, wherein said first, second and third sheets are flexible.

18. The fenestrated drape system of claim 1, wherein said third sheet is transparent.

19. The fenestrated drape system of claim 1, wherein at least one of said first or second sheets are transparent.

20. The fenestrated drape system of claim 1, wherein said third sheet is made from plastic.

21. The fenestrated drape system of claim 1, further comprising at least one strap configured to wrap around a body part.

22. The fenestrated drape system of claim 1, further comprising a tourniquet configured to control the blood flow to an injured area.

23. A fenestrated drape attachment comprising:
a first sheet having a first passthrough opening;
a second sheet adjacent to said first sheet;
at least one elastic cord coupling said second sheet to first sheet, wherein a first end of said at least one elastic cord is the only portion of said at least one elastic cord in contact with said second sheet; and
at least one pulling cord coupled to said second sheet so that the second sheet is configured to uncover said first passthrough opening when the at least one pulling cord is actuated, wherein said first and second sheets are configured to attach onto a drape having a fenestration so that the second sheet uncovers both said first passthrough opening and said fenestration when the at least one pulling cord is actuated; said second sheet being the only sheet provided between said first sheet and said drape having the fenestration.

24. The fenestrated drape system of claim 23, wherein the second sheet is configured to slide in relation to said first sheet to uncover both said first passthrough opening and said drape fenestration.

25. The fenestrated drape system of claim 23, wherein said second sheet returns to an original position covering both said first passthrough opening and said drape fenestration when the at least one pulling cord is not actuated.

26. The fenestrated drape system of claim 23, comprising two elastic cords coupling said second sheet to said first sheet.

27. The fenestrated drape system of claim 26, wherein second ends of the two elastic cords are respectively coupled to opposite locations of an end of said first sheet, and first ends of the two elastic cords are respectively coupled to opposite locations of an end of said second sheet.

28. The fenestrated drape system of claim 23, wherein a second end of said at least one elastic cord is coupled to an end of said first sheet.

29. The fenestrated drape system of claim 28, wherein said at least one pulling cord is coupled to another end of said second sheet, opposite to the end of the second sheet where said at least one elastic cord is coupled.

30. The fenestrated drape system of claim 23, wherein said at least one pulling cord is non-stretchable.

31. The fenestrated drape system of claim 23, wherein said at least one pulling cord comprises a handle configured to be manually actuated.

32. The fenestrated drape system of claim 23, further comprising a mechanical pulling mechanism coupled to said at least one pulling cord so that actuation of said mechanical mechanism by a user causes said at least one pulling cord to selectively cover and uncover both said first and second passthrough openings.

33. The fenestrated drape system of claim 32, wherein said mechanical pulling mechanism comprises a spool where said at least one pulling cord is wound.

34. The fenestrated drape system of claim 33, wherein said spool is coupled to a pedal.

35. The fenestrated drape system of claim 33, wherein said spool is coupled to a motor.

36. The fenestrated drape system of claim 35, wherein said motor is actuated at least by one of a wired actuator or a wireless actuator.

37. The fenestrated drape system of claim 35, wherein said at least one of a wired actuator or a wireless actuator is a pedal.

38. The fenestrated drape system of claim 31, wherein said handle comprises at least one of: a magnet, a carabiner, a hook and loop fastener, a clip or a hook.

39. The fenestrated drape system of claim 23, wherein said first and second sheets are flexible.

40. The fenestrated drape system of claim 23, wherein said second sheet is transparent.

41. The fenestrated drape system of claim 23, wherein said first sheet is transparent.

42. The fenestrated drape system of claim 23, wherein said second sheet is made from plastic.

43. The fenestrated drape system of claim 23, further comprising at least one strap configured to wrap around a body part.

44. The fenestrated drape system of claim 23, further comprising a tourniquet configured to control the blood flow to an injured area.

* * * * *